(12) United States Patent
Ciesielski et al.

(10) Patent No.: US 8,580,269 B2
(45) Date of Patent: *Nov. 12, 2013

(54) SURVIVIN PEPTIDES FOR AUTOIMMUNE THERAPIES

(75) Inventors: Michael J. Ciesielski, Orchard Park, NY (US); Robert A. Fenstermaker, Amherst, NY (US)

(73) Assignee: Health Research, Inc., Buffalo, NY (US)

( * ) Notice: Subject to any disclaimer, the term of this patent is extended or adjusted under 35 U.S.C. 154(b) by 102 days.

This patent is subject to a terminal disclaimer.

(21) Appl. No.: 13/100,564

(22) Filed: May 4, 2011

(65) Prior Publication Data

US 2011/0268755 A1 Nov. 3, 2011

Related U.S. Application Data

(63) Continuation-in-part of application No. 12/176,052, filed on Jul. 18, 2008, now Pat. No. 7,943,138.

(60) Provisional application No. 60/961,206, filed on Jul. 19, 2007, provisional application No. 61/331,130, filed on May 4, 2010.

(51) Int. Cl.
| | |
|---|---|
| *A61K 38/00* | (2006.01) |
| *A61K 38/17* | (2006.01) |
| *A61P 37/00* | (2006.01) |
| *A61P 37/04* | (2006.01) |
| *A61P 29/00* | (2006.01) |

(52) U.S. Cl.
USPC ............... 424/185.1; 424/810; 424/93.71; 514/18.9; 514/17.9; 514/16.6; 514/21.6; 514/21.5; 530/326; 530/327; 530/328; 530/868

(58) Field of Classification Search
None
See application file for complete search history.

(56) References Cited

U.S. PATENT DOCUMENTS

| | | |
|---|---|---|
| 2004/0176573 A1 | 9/2004 | Thor et al. |
| 2006/0073159 A1 | 4/2006 | Vonderheide et al. |
| 2007/0083334 A1 | 4/2007 | Mintz et al. |
| 2007/0104689 A1 | 5/2007 | Gillies et al. |

FOREIGN PATENT DOCUMENTS

| | | |
|---|---|---|
| WO | WO 2004/067023 | 8/2004 |
| WO | WO2006051075 | * 5/2006 |
| WO | WO2007039192 | * 4/2007 |

OTHER PUBLICATIONS

O. Simonetti, Expression of vascular endothelial growth factor, apoptosis inhibitors (survivin and p16) and CCL27 in alopecia areata before and after diphencyprone treatment: an immunohistochemical study, 2004, British Journal of Dermatology, 150:940-948.*
M.K Sharief, Heightened expression of survivin in activated T lymphocytes from patients with multiple sclerosis, 2001, Journal of Neuroimmunology 119:358-364.*
Maria Bokarewa, Balance between survivin, a key member of the apoptosis inhibitor family, and its specific antibodies determines erosivity in rheumatoid arthritis, 2005, Arthritis Res Ther, 7:R349-358.*
Ciesielski, et al. Antitumor effects of a xenogeneic survivin bone marrow derived dendritic cell vaccine against murine GL261 gliornas Cancer Immunology, vol. 55, No. 12, Feb. 17, 2006, pp. 1491-1503.
Bachinsky, et al. "Mapping and binding analysis of peptides derived from the tumor-associated antigen survivin for eight HLA alleles." Cancer Immunity 2005, vol. 5, 2005, p. 6.
Fenstermaker R A et al: "Immunotherapeutic strategies for malignant glioma", Cancer Control, H. Lee Moffitt Cancer Center and Research Institute, Tampa, US, vol. 11, No. 3, May 1, 2004, pp. 181-191.
Otto K et al: "Lack of toxicity of therapy-induced T cell responses against the universal tumour antigen survivin" Vaccine, vol. 23, No. 7, Jan. 4, 2005, pp. 884-889.
Ciesielski et al. "Therapeutic effect of a T helper cell supported CTL response induced by a survivin peptide vaccine against murine cerebral glioma", Cancer Immunology, vol. 57, No. 12, Apr. 26, 2008, pp. 1827-1835.
Ciesielski et al. "Antitumor cytotoxic T-cell response induced by a survivin peptide mimic", Cancer Immunology, vol. 59, No. 8, Apr. 27, 2010, pp. 1211-1221.

* cited by examiner

*Primary Examiner* — Julie Ha
*Assistant Examiner* — Erinne Dabkowski
(74) *Attorney, Agent, or Firm* — Hodgson Russ LLP

(57) ABSTRACT

Compositions and methods for stimulating an immune response against cells that express survivin are provided. The method is suitable for prophylaxis and/or therapy of autoimmune disorders. The method involves administering to an individual a composition that contains a survivin peptide mimic that has a cysteine to methionine alteration at amino acid position 57 of wild type survivin. Fragments of the peptides can also be used.

7 Claims, 7 Drawing Sheets

Figure 1.

AA49-ENEP<u>DLAQCFFCFKELEGW</u>EPDD-AA71  (Wild Type; SEQ ID NO:3)

| C to M change | | Wild type | |
|---|---|---|---|
| DLAQMFFCFKELEGW (SEQ ID NO:6) | = SVN53-67/M57 | DLAQCFFCFKELEGW (SEQ ID NO:18) | = SVN53-67 |
| AQMFFCFKEL (SEQ ID NO: 15) | = SVN55-64/M57 | AQCFFCFKEL (SEQ ID NO:19) | = SVN55-64 |
| QMFFCFKEL (SEQ ID NO:16) | = SVN56-64/M57 | QCFFCFKEL (SEQ ID NO:20) | = SVN56-64 |
| MFFCFKEL (SEQ ID NO:17) | = SVN57-64/M57 | CFFCFKEL (SEQ ID NO:11) | = SVN57-64 |

DLAQMFFCFKELEGW
(SEQ ID NO:6)  } — MHC class II ligand

AQMFFCFKEL
(SEQ ID NO:15)
QMFFCFKEL
(SEQ ID NO:16)
MFFCFKEL
(SEQ ID NO:17)  } — MHC class I ligands
(also contained within SVN53-67)

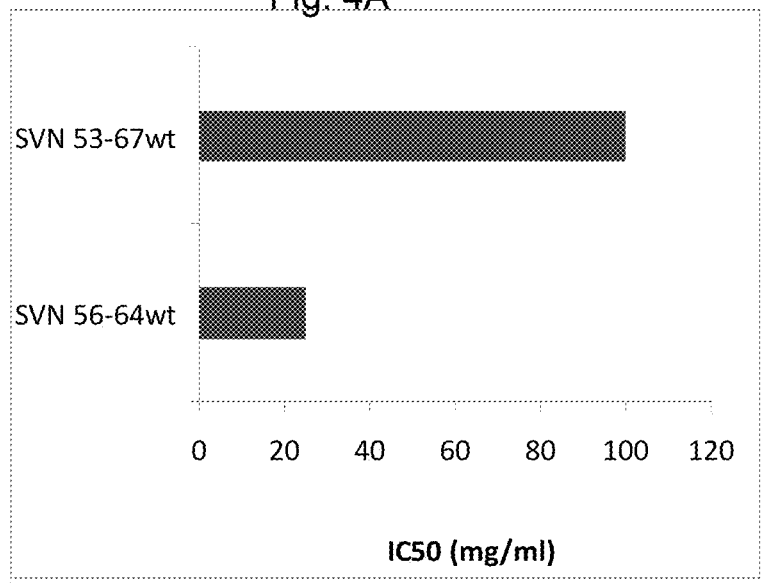
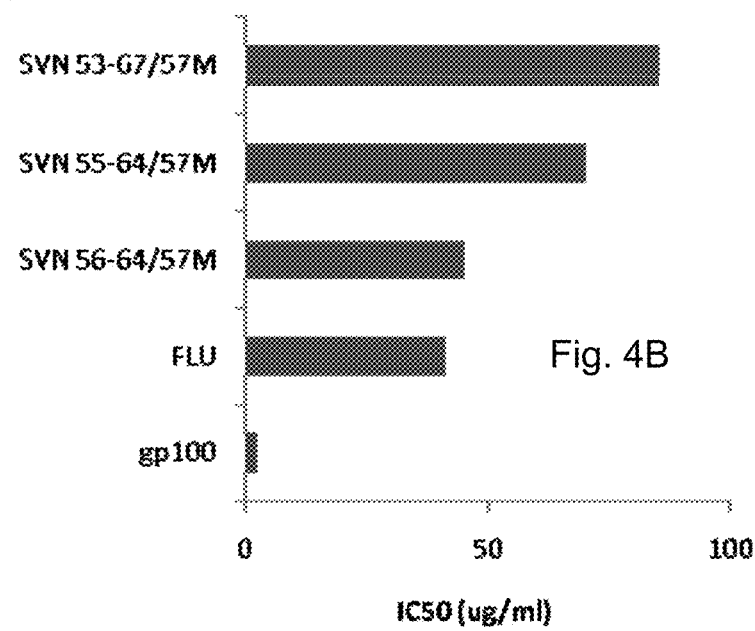

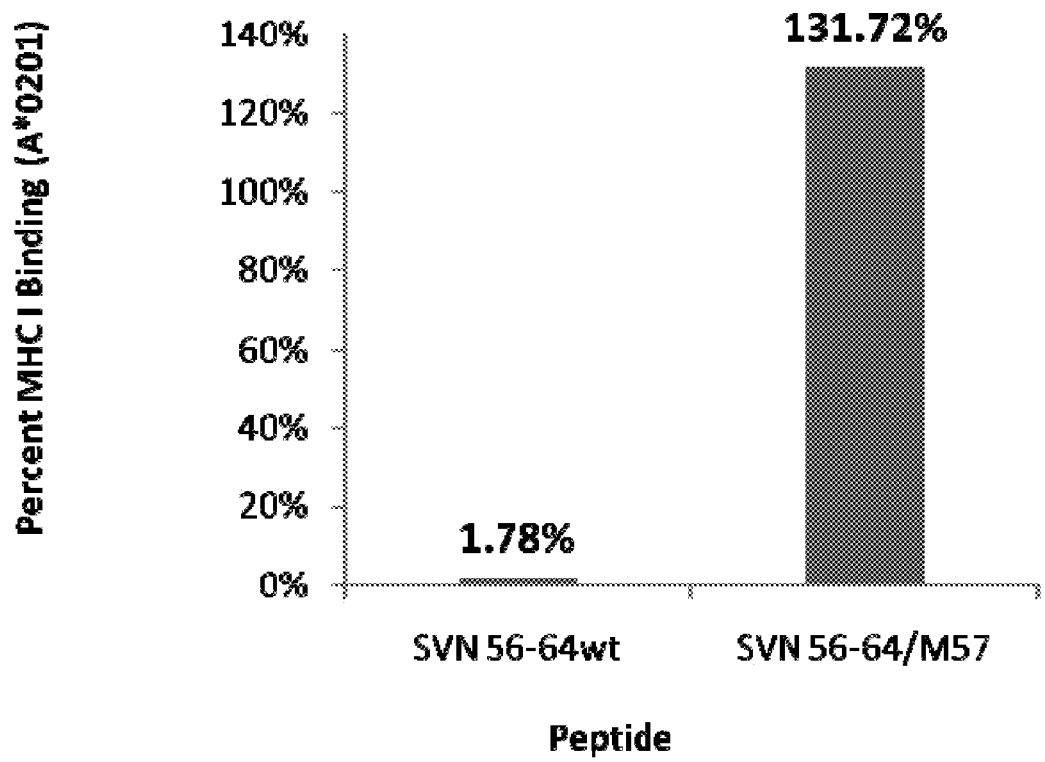

SURVIVIN PEPTIDES FOR AUTOIMMUNE THERAPIES

CROSS-REFERENCE TO RELATED APPLICATIONS

This application is a continuation-in-part of U.S. application Ser. No. 12/176,052, filed Jul. 18, 2008, which in turn claims priority to U.S. application No. 60/961,206, filed Jul. 19, 2007, the disclosures of which are incorporated herein by reference. This application also claims priority to U.S. application No. 61/331,130, filed May 4, 2010, the disclosure of which is incorporated herein by reference.

FIELD OF THE INVENTION

The present invention relates generally to autoimmune diseases and more specifically to prophylaxis and/or therapy for autoimmune diseases using compositions comprising modified survivin peptides.

BACKGROUND OF THE INVENTION

Survivin is a 16.5 kDa intracellular protein that belongs to the inhibitor of apoptosis protein (IAP) family. Survivin acts in concert with the mitotic spindle apparatus to regulate cell division. It is expressed in certain cells during the G2/M phase of the cell cycle and associates with the spindle microtubule organizing center during this phase of cell cycle progression [Zhao J, et al. (2000) J Cell Sci, 113:4363-71; Li F, et al. (1998) Nature, 396:580-4; Fortugno P, et al. (2002) J Cell Sci, 115:575-85]. Survivin has also been shown to modulate the function of certain caspases, directly inhibiting apoptosis [Tamm I, et al. (1998) Cancer Res, 58:5215-20; Conway et al. (2000) Blood 95:1435-42; Shin S, et al. (2001) Biochemistry, 40:1117-23]. In addition, survivin inhibits the cyclin D/cdk4 complex [Fukuda S, Pelus L M. (2002) Cell Cycle, 1(5):322-6], permitting cell cycle progression. Thus, survivin functions in critical roles at a number of different cellular loci to regulate the cell cycle and to inhibit apoptotic cell death.

Survivin is overexpressed during the G(2)/M phase of the cell cycle in most cancer cells and is one of the most specific cancer antigens identified to date. It is expressed in a large percentage of tumors and is rarely detectable in normal adult tissues [Overwijk W W, et al. (1998) J Exp Med, 188:277-86; Adida C, et al. (1998) Am J Pathol 152:43-49]. Although survivin is expressed in some instances within CD34(+) hematopoietic stem and progenitor cells that have been stimulated by hematopoetic growth factors, it is generally not presented on the surface of these cells. [Fukuda S, Pelus L M. (2002) Cell Cycle. 1(5):322-6].

It has recently come to light that survivin-expressing cells that mediate autoimmune processing (SECMAPs), such as synovial cells, are involved in certain autoimmune disorders express survivin in their pathogenic state. Examples of such cells include but are not necessarily limited to macrophages, T cells and fibroblasts. Autoimmune disorders that have been positively correlated with the presence of SECMAPs include but are not necessarily limited to arthritis, and particularly rheumatoid arthritis, and multiple sclerosis (see, for example, for arthritis: Smith, et al. Rheumatology (Oxford). 2010 Feb. 10. [Epub ahead of print]; Svensson et al. Ann Med. 2010; 42(1):45-54; Baran et al., J Cell Mol Med. 2009 Feb. 27. [Epub ahead of print]; Dharmapatni et al., Arthritis Res Ther. 2009; 11(1):R13; et al. Clin Exp Rheumatol. 2008 September-October; 26(5):881-6; Galeotti et al., Clin Exp Rheumatol. 2008 March-April; 26(2):373-8; Gagarina et al. J Biol Chem. 2008 Jan. 4; 283(1):648-59; Bokarewa et al. Scand J. Immunol. 2007 August-September; 66(2-3):192-8; Markham et al. Br J. Dermatol. 2006 December; 155(6): 1191-6; Hanashi et al. Clin Exp Rheumatol. 2005 July-August; 23(4):550; Bokarewa et al. Arthritis Res Ther. 2005; 7(2):R349-58; and for multiple sclerosis: Hebb et al. Mult Scler. 2008 June; 14(5):577-94; Sharief et al. Eur J. Neurol. 2002 September; 9(5):503-10; Sharief et al. Arch Neurol. 2002 July; 59(7):1115-21; Sharief et al. J. Neuroimmunol. 2001 Oct. 1; 119(2):358-64).

Thus, there is an ongoing and unmet need for compositions and methods for prophylaxis and/or therapy of autoimmune disorders that are caused and/or sustained at least in part by the activity of SECMAPs.

SUMMARY OF THE INVENTION

The present invention provides compositions and methods for stimulating an immune response against cells that express survivin. The method in one embodiment provides for prophylaxis and/or therapy of one or more autoimmune disorders. The method comprises administering to an individual a composition comprising a survivin peptide mimic that contains a cysteine to methionine alteration at amino acid position 57 of wild type survivin. The peptides used in the invention are 9-23 amino acids in length and contain the sequence ENEPDLAQMFFCFKELEGWEPDD (SEQ ID NO:4), or contain a a fragment of SEQ ID NO:4. The fragments comprises at least 9 contiguous amino acids of SEQ ID NO:4, and further comprises SEQ ID NO:5 (QMFFCF). The compositions and methods of the invention are demonstrated to be effective in stimulating an immune response against human survivin-expressing immune cells, such as malignant human immune cells (lymphoma) and human chronic lymphocytic leukemia (CLL) cells.

BRIEF DESCRIPTION OF THE FIGURES

FIG. 1 provides a summary of wild type and altered peptide sequences utilized in the present invention.

FIG. 2 also depicts a peptide consisting of the sequence DLAQMFFCFKELEGW (SEQ ID NO:6). Also shown is the sequence DLAQCFFCFKELEGW which consists of amino acid number 5 through amino acid number 19 of SEQ ID NO:3.

FIGS. 4A, 4B and 4C provide a graphical representations of data from an analysis of HLA-A*0201 binding properties of survivin peptides. To obtain the data summarized in FIGS. 4A and 4B, survivin peptide epitopes were used in MHC class I peptide competitive displacement assays. IC50 represents the 50% inhibition concentration of survivin peptide required to displace a fluorescently labeled-known human MHC Class I ligand (HPV18-27). Positive control peptides (Flu & gp100) represent known immunogenic MHC class I ligands. Data represent mean fluorescence±S.E.M. of triplicate samples. FIG. 4C provides a graphical representation of data for specific HLA-A*0201 pentamer binding of wild type and altered survivin peptide epitopes.

FIG. 6 demonstrates that the peptide SVN57-64/M57 DC vaccine enhances survival over the wild type peptide in the GL261-057BL/6 glioma model.

DESCRIPTION OF THE INVENTION

Figure 2:
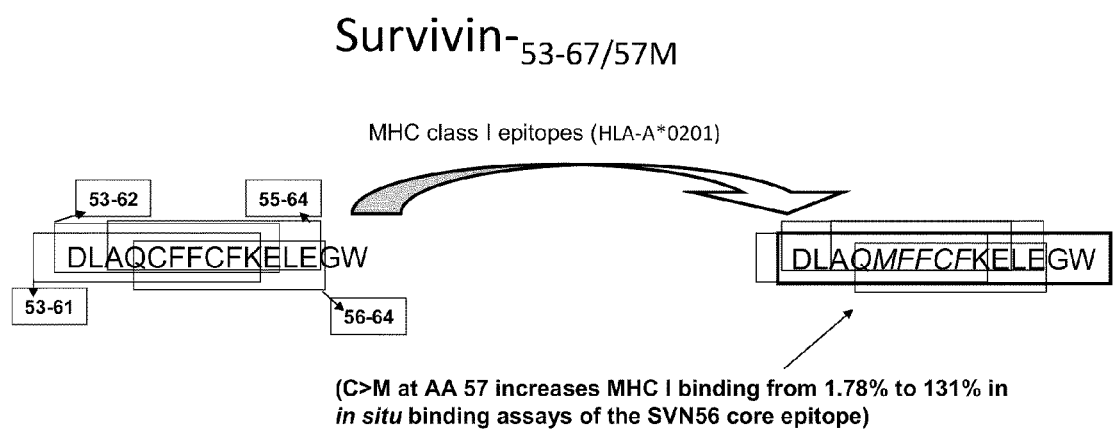
FIG. 2 provides a graphical comparison of wild type and altered peptide sequences showing MHC class I (HLA-A*0201) epitopes in boxes. A sequence common to all the peptides of the invention (QMFFCF) (SEQ ID NO:5) is italicized in Survivin-53-67/57M.

The present invention provides compositions and methods for prophylaxis and/or therapy of one or more disorders that are positively associated with cells that express survivin. In one embodiment, the disorder is an autoimmune disorder. In various embodiments, the autoimmune disorders are caused by and/or are positively correlated with the presence of SECMAPs. Examples of SECMAPs include but are not necessarily limited to survivin-expressing lymphocytes, B cells, T cells, macrophages, monocytes, and other types of cells that participate in immunological responses and express survivin. We demonstrate the method of the invention by effective stimulation of an immune response against survivin expressing lymphocytes (CNS lymphoma cells).

In one embodiment, the SECAMPs are synovial cells, which are generally considered to refer to a cell physiologically associated with the synovial membrane or present in the subsynovial space, or a cell obtained from a joint's synovial membrane or synovial fluid. Synovial cells include mesenchymal cells, fibroblasts, fibroblast-like cells, macrophages, de-differentiated chondrocytes, synovial lining cells, synovial fibroblast-like cells, and T cells that reside in the synovium.

The compositions comprise survivin peptide mimics that contain a cysteine to methionine alteration at amino acid position 57 of the wild type survivin protein sequence. The complete amino acid sequence of human and mouse survivin proteins are provided as SEQ ID NO:1 and SEQ ID NO:2, respectively. The human and mouse sequences are 100% homologous between amino acids 31 and 71. The peptides are 9-23 amino acids in length and have the sequence of SEQ ID NO:4 (ENEPDLAQMFFCFKELEGWEPDD) or a fragment thereof, wherein the fragment comprises at least 9 contiguous amino acids of SEQ ID NO:4, and wherein the fragment also comprises the sequence of SEQ ID NO:5 (QMFFCF). The peptides are capable of stimulating an improved human cell mediated immune response against survivin-expressing synovial cells, as compared to the cell mediated immune response elicited by peptides having the wild type survivin sequence. Thus, the compositions and methods of the invention have already been established for use in enhancing an immune response against survivin-expressing cells, such as malignant immune cells (lymphoma) and this capability is expected to be useful against synovial cells that also express survivin, wherein the presence of the survivin-expressing synovial cells is positively correlated with an autoimmune disease.

The method of the invention comprises administering a composition comprising a peptide of the invention to an individual so that an immune response against survivin-expressing cells in the individual is stimulated. In one embodiment, the individual in which the survivin-expressing cells are present in an individual who has been diagnosed with or is suspected of having a disorder that is positively correlated with the presence of survivin-expressing cells. In one embodiment, the method of the invention comprises administering a composition comprising a peptide of the invention to an individual diagnosed with or suspected of having an autoimmune disorder that is positively correlated with the presence of survivin-expressing cells. In one embodiment, the survivin-expressing cells are SECAMPs. Also provided is a substantially purified population of mammalian dendritic cells that are loaded with a peptide of the invention.

In connection with the present invention, survivin has been implicated as a valid target in a number of autoimmune disorders. Specific types of autoimmune disorders that have been shown to involve survivin-expressing cells include: Rheumatoid Arthritis, Multiple Sclerosis, Systemic Sclerosis, Diabetes, Colitis and Hepatic Cirrhosis. In each instance survivin has been implicated in the ability of a cell to evade its own programmed cell death pathway (apoptosis). In terms of autoimmune disease, insufficient apoptosis is believed to provide a mechanism for cells (B cells, T cells, natural killer (NK) cells, macrophages, fibroblasts etc.) to continue self-reactive tissue destruction via a response that normally would have been downregulated. Without intending to be constrained by theory, in Rheumatoid Arthritis this is thought to be manifested through B and T cells that may have arisen in response to viral infection, however once the infection is cleared the immune response does not downregulate. Thus, highly differentiated immune cells can damage healthy tissue via cross-reactive mechanisms. Survivin has also been found to be a potential prognostic factor related to the severity of Rheumatiod Arthritis in these cases. Anti-survivin antibodies have also been shown to be produced in neurodegenerative disease (Multiple Sclerosis, Systemic Sclerosis). In diabetes abnormal beta pancreatic islet cells were found to express survivin, while in normal (non-diabetic) cases these cells did not express survivin. Colitis can lead to a predisposition for colon cancer and colonic hyperplastic epithelium express survivin. In addition survivin is upregulated in cells within hepatic cirrhosis. Additional studies have shown molecular regulation of survivin in immune cells related to autoimmune disease. In multiple sclerosis, T lymphocytes previously shown to express high levels of survivin, will down-regulate survivin upon exposure to interferon beta-1a (a current therapy for MS). These cells subsequently apoptose which is correlated with clinical response.

Collectively these data are believed to represent two pathways of survivin-related pathogenesis: 1) Through direct overexpression of survivin in target tissues (inflamed fibroblasts, epithelium, etc.) abnormal cells are attacked by the immune system, however this response is ineffective (producing primarily antibodies) which leads to a chronic inflammatory state such as observed in RA and colitis. It is expected that the present invention will lead to improved elimination of the abnormal survivin-expressing cell and thus alleviate damaging chronic inflammation. 2) Overexpression of survivin within the immune cell itself (B cell, T cell etc.) can lead to an immune response that may continue to damage normal tissues long after the original target cell had been eliminated. These non-apoptosing immune cells would be expected to be destroyed by the present invention, thus reducing their capacity to participate in auto-immune disorders. Further, our own laboratory studies have demonstrated the ability of the vaccine's ability to induce anti-B cell responses (in CNS lymphoma and CLL) which shown the utility of the SVN53-67/M57 peptide for use in a multitude of diseases other than cancer, such as autoimmune disorders.

Thus, in view of the foregoing, it will be recognized by the skilled artisan that the method is expected to be useful for therapy and/or prophylaxis of a wide range of autoimmune disorders, non-limiting examples of which include Acute disseminated encephalomyelitis (ADEM), Alzheimers Disease, alopecia greata, ankylosing spondylitis, aneurysms, arthritis, antiphospholipid antibody syndrome, Addison's Disease, autoimmune hemolytic anemia, Meniere's Disease, autoimmune lymphoproliferative syndrome (ALPS), thrombocytopenic purpura, autism, pediatric autoimmune neuropsychiatry disorders (PANDAS), hemolytic anemia, autoimmune hepatitis, autoimmune oophoritis, Behcet's disease, bullous pemphigoid, autoimmune cardiomyopathy, Crohn's disease, chronic fatigue syndrome, dermatomyositis, autoimmune diabetes mellitus (type 1), autoimmune epilepsy, Kawasaki's Disease, autoimmune glomerulonephritis, Graves' Disease, Goodpasture's syndrome, Guillain-Barré syndrome, inflammatory bowel disease, lupus nephritis, multiple sclerosis, myasthenia gravis, autoimmune myocarditis, Parkinson's Disease, pemphigus, pernicious anemia, polyarteritis nodosa, polymyositis, primary biliary cirrhosis, psoriasis, rheumatic fever, rheumatoid arthritis and juvenile rheumatoid arthritis, sarcoidosis, scleroderma, Sjögren's syndrome, systemic lupus erythematosus, autoimmune thyroiditis, ulcerative colitis, uveitis, vitiligo, Wegener's granulomatosis and autoimmune Wilson's Disease.

The method of the invention is expected to be effective in prophylaxis and/or therapy of autoimmune diseases as evidenced by factors that will be evident to those skilled in the art given the benefit of the present disclosure. For example, it is expected that by performing the method of the invention, the number, amount, sustenance, activation, etc. of survivin-expressing cells such as SECAMPs in the individual will be reduced. Detection and quantification of survivin-expressing cells can be performed using methods known to those skilled in the art.

By performing the method of the invention, it is expected that the severity of indicia of the particular disorder associated with the presence of survivin-expressing cells will be reduced and/or inhibited. For example, in the case of arthritis, inflammation, swelling, and/or pain in the affected joints or organs of the individual may be reduced, or the development of such symptoms may be inhibited or prevented. Reduction of other disease characteristics that will be apparent to the skilled artisan may also be affected and observed using conventional techniques. Similarly, in the case of multiple sclerosis, it is expected that the invention will facilitate prophylaxis and/or therapy of at least some multiple sclerosis symptoms, which include but are not necessarily limited to vision impairments, motor symptoms, including but not limited muscle weakness, ataxia, spasticity, slurred speech, muscle atrophy, dysfunctional reflexes, and combinations thereof, sensory impairments, bowel, bladder and sexual symptoms, and cognitive symptoms, including but not limited to short-term and long-term memory problems, dementia and mood swings.

It is expected that the method of the invention will stimulate a cell mediated immune response to survivin-expressing cells, such as SECAMPs. In connection with generation of cell mediated immunity, it is considered that a robust cellular immune response generally requires a peptide epitope to be displayed at the surface of an antigen presenting cell (APC) bound to MHC class I molecule, which can trigger a CD8+ T cell response (cytotoxic T cell or CTL). To sustain itself, the CTL immune response is preferably supported through presentation of peptide epitopes bound to MHC class II molecules to cytokine-secreting CD4+ T cells (T helper cells). While some survivin peptides have been shown to elicit CTL responses, attempts to provide viable peptide vaccine candidates from the region of survivin from amino acid numbers 53-67 have failed, possibly due to a lack of HLA*0201 binding ability [Bachinsky M M, et al. (2005) Cancer Immun. 22; 5:6].

The present invention overcomes these and other limitations by providing peptides derived from wild type survivin sequence, wherein the peptides comprise an altered amino acid sequence that improves MHC I binding properties so that the peptides are more effective than wild type peptides at eliciting human CTL responses against survivin-expressing cancer cells.

The complete amino acid sequence of human and mouse survivin proteins are known. The human and mouse sequences are 100% homologous between amino acids 31 and 71.

The peptides provided in the invention are fragments of full length survivin. The fragments and can range in size from 9-23 amino acids. SEQ ID NO:3 (ENEPDLAQCFFCFKELEGWEPDD) consists of wild type survivin amino acids 49-71.

Each 9-23 amino acid peptide of the invention comprises a cysteine to methionine (C to M) change at amino acid position 57 of the wild type survivin protein sequence. SEQ ID NO:4 (ENEPDLAQMFFCFKELEGWEPDD) is a 23 amino acid peptide consisting of wild type survivin amino acids 49-71, but for a C to M alteration at amino acid position 57 of full length survivin (the C to M alteration is present at amino acid number 9 of SEQ ID NO:4). The peptides of the invention can consist of from 9-23 contiguous amino acids of SEQ ID NO:4, including all integers between 9-23 amino acids, wherein the peptides include the C to M alteration at amino acid position 57 of full length survivin. Each peptide of the invention also comprises the core sequence of SEQ ID NO: 5 (QMFFCF). Representative survivin peptides and nomenclature used herein for the peptides are provided in FIG. 1.

Some non-limiting examples of peptides provided by the invention are also depicted in FIG. 2, wherein the core epitope sequence of SEQ ID NO:5 is shown boxed and italicized in context of longer suitable peptide sequences, also boxed, in the peptide shown on the right of FIG. 2. Accordingly, each of the boxed sequences that include the italicized core sequence are sequences of peptides included within the scope of the invention.

In one embodiment, a peptide of the invention consists of SEQ ID NO:6 (DLAQMFFCFKELEGW). This peptide is referred to alternatively as "SVN53-67/M57", "Survivin M57" and "M57." SVN53-67/M57 contains epitopes for binding human MHC I molecules and epitopes capable of binding human MHC II molecules to elicit CD4+ helper T cell responses.

Without intending to be bound by any particular theory, it is believed that the change of C to M in the peptides of the present invention allows for improved presentation of the MHC I binding epitopes to the human immune system, in part via more effective anchoring to MHC I, resulting in a longer association period between the peptide, the MHC I molecule and possibly T cell receptors, and thus, a more robust immune response. Shorter peptides can bind MHC I exclusively. Larger peptides, such as the 15-mer SVN53-67/M57, are designed to bind MHC class II, in addition to MHC class I.

We demonstrate that the C to M amino acid substitution in SVN53-67/M57 increases MHC I binding by approximately 73 fold in in situ binding assays for HLA-A*0201 relative to the wild type sequence (summarized FIG. 2 and FIG. 4C). We have also determined that peptides comprising the C to M change can be used to effectively stimulate CD8+ CTLs, to stimulate CD4+ T cell derived cytokine support, to enhance survival (and potentially be curative for glioma) in a mouse model of brain cancer, as well as elicit a strong ex vivo lytic response against human glioma and CNS lymphoma specimens. Therefore, it is expected that the peptides of the invention can be used in methods for eliciting enhanced MHC-I binding and improved CTL activity against survivin-expressing synovial cells when used as a vaccine in vivo in humans because of concomitantly improved association between the epitopes of the processed peptide and MHC-I anchor residues.

SVN 53-67 peptides (with or without the C to M change) are expected to bind numerous MHC Class I & II molecules that collectively represent a large patient population (Table 1).

TABLE 1

| MHC Class I | | MHC Class II |
|---|---|---|
| HLA-A*0201 | HLA-B*08 | HLA-DRB1*0301 (DR17) |
| HLA-A*03 | HLA-B*1501 (B62) | HLA-DRB1*0401 (DR4Dw4) |
| HLA-A*1101 | HLA-B*1510 | HLA-DRB1*0701 |
| HLA-A*2402 | HLA-B*18 | HLA-DRB1*1501 (DR2b) |
| HLA-A*2402 | HLA-B*2705 | |
| HLA-A*26 | HLA-B*2709 | |
| HLA-A*6801 | HLA-B*3901 | |
| HLA-B*0702 | HLA-B*4402 | |
| HLA-B*08 | HLA-B*5101 | |
| HLA-B*1402 | | |

The peptides of the invention can be prepared by any technique known to those skilled in the art or by techniques hereafter developed. For example, the peptides can be prepared using the solid-phase synthetic technique (Merrifield, J. Am. Chem. Soc., 15:2149-2154 (1963); M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985). The synthesis of peptides by solution methods may also be used, as described in The Proteins, Vol. II, 3d Ed., p. 105-237, Neurath, H., et al., Eds., Academic Press, New York, N.Y. (1976). The synthesized peptides may be substantially purified by preparative high performance liquid chromatography or other comparable techniques available in the art. The composition of the synthetic peptides can be confirmed by an technique for amino acid composition analysis.

The peptides of the present invention may be formulated with a suitable adjuvant in order to enhance the immunological response. Suitable adjuvants include but are not limited to mineral salts, including aluminium hydroxide and aluminium and calcium phosphate gels, oil emulsions and surfactant based formulations, saponin, AS02 [SBAS2] (oil-in-water emulsion), Montanide ISA-51 and ISA-720, particulate adjuvants, including virosomes, ASO4, [SBAS4] Al salt with MPL, ISCOMS (structured complex of saponins and lipids), polylactide co-glycolide (PLG), natural and synthetic microbial derivatives, lipoidal immunostimulators OM-174 (lipid A derivative), synthetic oligonucleotides containing immunostimulatory CpG motifs, modified bacterial toxins, endogenous human immunomodulators, including hGM-CSF and hIL-12, hIL-15, hIL-17, hIL-21, Immudaptin and inert vehicles, including gold particles. The peptides can be administered in a conventional dosage form prepared by combining the peptides with a standard pharmaceutically acceptable carrier according to known techniques. Some examples of pharmaceutically acceptable carriers can be found in: *Remington: The Science and Practice of Pharmacy* (2005) 21st Edition, Philadelphia, Pa. Lippincott Williams & Wilkins.

In one embodiment, the peptides of the invention may be conjugated to an immunogenic carrier protein. Suitable carriers include but are not limited to Limulus polyphemus hemocyanin (LPH), Tachypleus tridentatus hemocyanin (TTH), and bovine serum albumin (BSA), tetanus toxoid and diphtheria toxin, DHBcAg, polyribotol ribosyl phosphate (PRP), PncPD11, and nanoparticle formulations.

In one embodiment, a suitable immunogenic carrier protein is Keyhole Limpet Hemocyanin (KLH).

The peptides of the invention may also be administered as peptide loaded dendritic cells. Thus, the method includes administering to the individual dendritic cells that have been incubated with a peptide of the invention such that the dendritic cells have taken up the peptide to obtain peptide loaded dendritic cells that facilitate presentation of MHC epitope(s) present in the peptide. The dendritic cells employed for this purpose may be isolated from the individual to whom they are to be delivered after incubation with the peptide, or they may be obtained from an allo-matched individual. Accordingly, the invention also provides a composition comprising a substantially purified population of mammalian dendritic cells, wherein the dendritic cells have been incubated with a peptide of the invention such that the dendritic cells take up the peptide.

Various methods known to those skilled in the art may be used to introduce the compositions of the invention to an individual. These methods include but are not limited to intracranial, intrathecal, intradermal, intramuscular, intraperitoneal, intravenous, subcutaneous, oral and intranasal routes.

It will be recognized by those of skill in the art that the form and character of the particular dosing regime employed in the method of the invention will be dictated by the route of administration and other well-known variables, such as the size of the individual and the stage of the disease. Based on such criteria, one skilled in the art can determine an amount of peptide effective to inhibit growth of SECAMPs for any particular individual and for any particular autoimmune disorder. It is generally considered that the amount of peptide administered will range from microgram to milligram amounts.

The method of the invention can be performed in conjunction with conventional autoimmune therapies. The compositions of the invention can be administered prior to, concurrently, or subsequent to such therapies.

The following Examples are meant to illustrate, but not to limit the present invention.

Example 1

This Example provides an in vitro analysis of selected survivin peptide epitopes predicted by SYFPEITHI analysis to bind MHC class I molecules (Table 2). Peptide synthesis was performed using Fmoc chemistry and a solid support resin (Sigma-Genosys, The Woodlands, Tex.). Each peptide was stored at −20° C. until use and diluted in DMSO. An ovalbumin (OVA) peptide sequence SIINFEKL was used as a control. Positive control peptide (OVA-258) represents a known immunogenic MHC class I ligand with a score indicating strong potential binding. Underlined amino acid residues represent MHC I anchor positions.

TABLE 2

| Predicted H-2K$^b$ Binding position | Epitope | Score |
|---|---|---|
| OVA-258 | S I <u>I</u> N F E K L (SEQ ID NO: 7) | 25 |
| SVN-9 | A W <u>Q</u> P F L K D (SEQ ID NO: 8) | 12 |
| SVN-18 | R I <u>S</u> T F K N W (SEQ ID NO: 9) | 13 |
| SVN-39 | A E <u>A</u> G F I H C (SEQ ID NO: 10) | 12 |
| SVN-57-64 | C F <u>F</u> C F K E L (SEQ ID NO: 11) | 20 |
| SVN-57-64/M57 | M F <u>F</u> C F K E L (SEQ ID NO: 17) | 20 |
| SVN-82 | S G <u>C</u> A F L S V (SEQ ID NO: 12) | 18 |
| SVN-L82 | L G <u>C</u> A F L S V (SEQ ID NO: 13) | 18 |
| SVN-97 | T L <u>G</u> E F L K L (SEQ ID NO: 14) | 22 |

Figure 3:
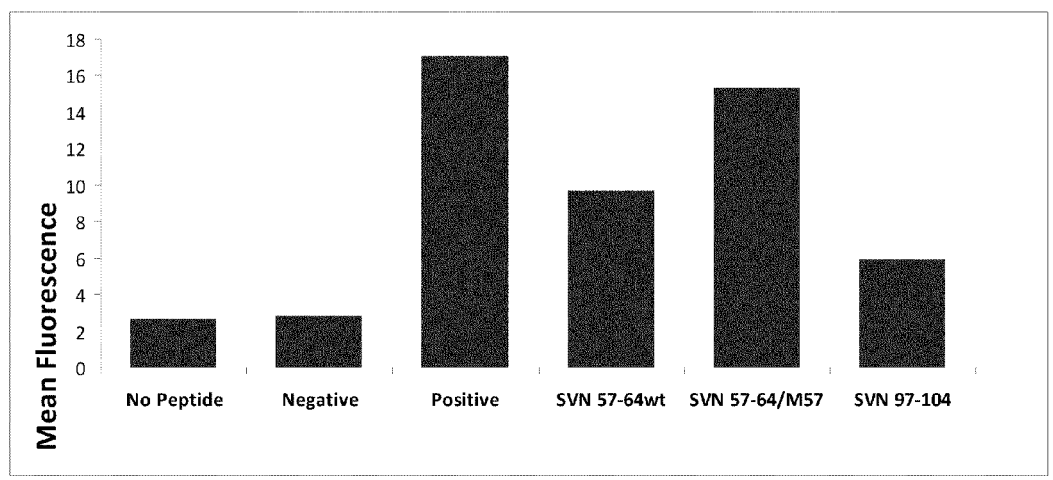
FIG. 3 provides a graphical representation of in vitro test data obtained from survivin peptide binding assays.

In vitro test data for peptide binding assays is presented in FIG. 3. To obtain the data presented in FIG. 3, survivin peptide epitopes were used in conventional MHC class I peptide binding assays. Mean fluorescence in FIG. 3 represents binding of SVN peptides to H2-K$^b$. Upregulation of H2-K$^b$ molecules on the surface of murine RMA-S cells which are deficient in the expression of surface MHC class I molecules was used to determine actual survivin peptide binding in vitro. Data presented in FIG. 3 represent the binding of 100 μM peptide at 37° C. The negative control is an irrelevant peptide that does not bind MHC class I. Data represent mean fluorescence±S.E.M. of triplicate samples.

As can be seen from the data presented in FIG. 3, computer analysis is insufficient to reliably predict the effect of altered peptide sequences on MHC binding strength. Notably, SVN$_{97-104}$ is a peptide that is currently in clinical trials but exhibits binding that is less than SVN 57-64 wt, and considerably less than SVN 57-64/M57, despite the data in Table 2 indicating SVN$_{97-104}$ should exhibit stronger binding than either the wild type or mutant SVN 57-64 peptide. Further, while other changes to amino acids may also enhance binding, we have determined that changes to amino acid anchor positions 57, 59, and 64 (including the changes 57C>L, 59F>Y, and 64L>V) do not improve the immune response to the peptides, despite computer analysis predicting improved MHC retention compared to the wild type sequence. Additionally, we have also determined that the mere substitution of a methionine for an amino acid in the MHC class I first anchor position does not necessarily result in enhanced survivability in a mouse model of intracranial glioma, as evidenced by our analysis of a survivin nonapeptide comprising an S to M change at survivin amino acid position 82.

Example 2

This Example demonstrates enhanced MHC class I binding of the peptides of the invention relative to wild type peptides, and also demonstrates that the method of the invention can elicit an enhanced cell mediated immune response against human cancer cells that express survivin, including against non-glioma cancer cells.

Without intending to be bound by any particular theory, it is considered that SVN53-67/M57 and SVN53-67 exhibit similar survival profiles in C57BL/6 mice due to the M57 alteration not lying in an anchor position relative to the mouse H-2 Kb molecule. As such, both peptides will bind H-2 Kb (the murine MHC class I counterpart) to a similar extent in mice. The observation that SVN53-67/M57 retains the wild type immunogenic response in mice despite containing an alerted human epitope indicates that it is an effective peptide mimic (despite the fact that such an amino acid alteration could be expected to negatively impact immunity due to disruption of the interaction with the T cell receptor) and that the C to M alteration does not impart deleterious effects when SVN53-67/M57 is used as a vaccine. However, it is in administration to humans that the peptides of the invention are expected to display their enhanced potential, since the alteration of 57C to M alters the wild type peptide so that it contains a sequence that facilitates improved interaction with human MHC I. This is supported by the disparate MHC class I binding characteristics of the wild type and M57 peptides (FIG. 4A-C). As determined by competitive peptide binding assays, SVN53-67/M57 binds HLA-A*0201 approximately 12 fold stronger than the wild type SVN53-67 (FIG. 4A-B). Moreover utilizing a survivin/MHC Class I-specific pentamer, the core peptide SVN56-64/M57 binds HLA-A*0201 approximately 73 fold stronger than the wild type SVN56-64 (FIG. 4C). Collectively, this signifies that the C>M alteration leads to enhanced affinity of peptide mimic for the MHC class I molecule relative to the wild type survivin sequence. Thus, the C to M change elicits a profound improvement in MHC class I binding over the wild type sequence. This improvement would be expected to result in enhanced CTL activation against autologous cancer cells. It is accordingly noteworthy that, according to our data, as compared to the wild type peptide, SVN53-67/M57 elicits a 3 to 5 fold increase in CTL mediated killing against allogeneic HLA-matched human glioma, autologous human glioma and further agains autologous human lymphoma cells (FIG. 5), demonstrating that the method of the invention can elicit a cell mediated immune response that is significantly improved over that induced by peptides having a wild type sequence. (See FIG. 6 demonstrating the in vivo efficacy of the invention against glioma). Moreover, we have shown that the method of the invention can elicit a cell mediated immune response against human cancer cells other than glioma (see Example 3). Thus, the method is expected to have broad applicability against all types of cells that express survivin, including survivin-expressing synovial cells.

Example 3

This Example demonstrates ex vivo T cell stimulation using survivin-loaded autologous human dendritic cells challenged with autologous human CNS lymphoma cells.

Figure 5:
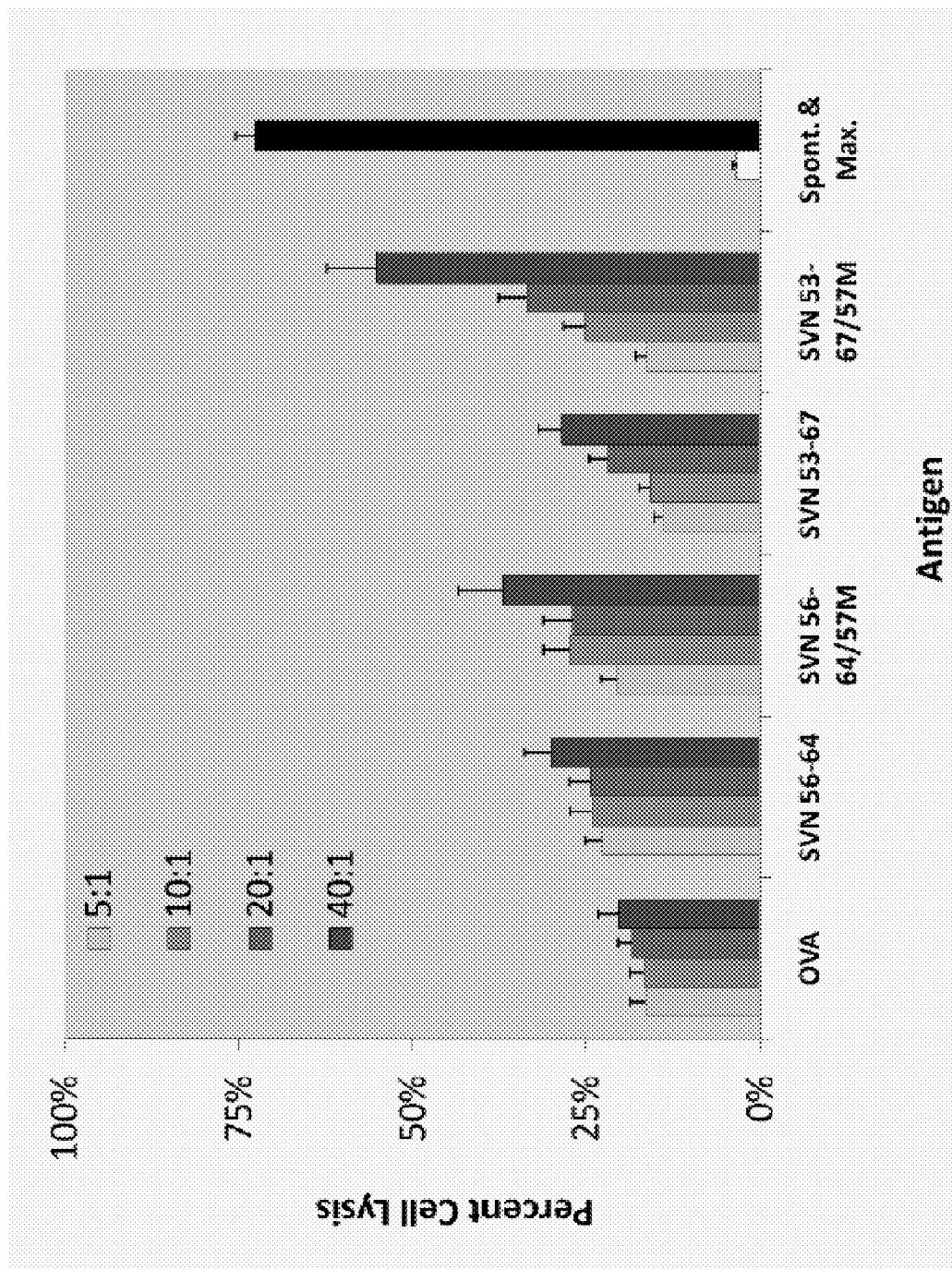
FIG. 5 provides a graphical representation of data obtained from ex vivo T cell stimulation via survivin-loaded autologous dendritic cells challenged with autologous CNS Lymphoma (HLA-A*2901, HLA-A*3002; Auto).
Figure 6:
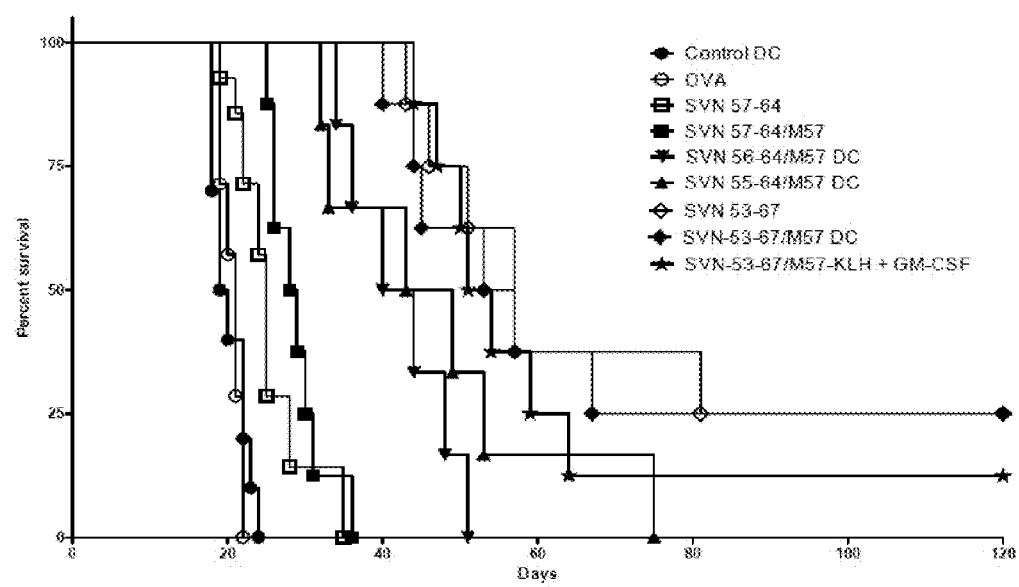
FIG. 6 provides a graphical representation of data obtained from intracranial survival studies in a GL261 murine model utilizing altered peptides based on survivin amino acids 53-67. The peptides were administered using peptide loaded dendritic cell (DC) vaccines or as Keyhole Limpet Hemocyanin (KLH) conjugates. To obtain the data presented in FIG. 6, mice were intracranially implanted with $1 \times 10^5$ GL261 cells and were treated with survivin peptide DC vaccines. C57BL/6 mice were immunized with SVN57-64 based altered peptides, or OVA258-265 peptide loaded DC2.4 cells as well as a direct subcutaneous injection of 100 ug SVN 53-67/M57-KLH peptide in Incomplete Freund's Adjuvant (IFA) plus 100 ug GM-CSF. Vaccinations began 4 days after tumor cell implantation and were repeated (boosted) every 7 days to simulate a therapeutic setting. Survival was plotted according to Kaplan-Meier methods. Long-term survivors were confirmed tumor-free by high field strength MRI.

To produce the data presented in FIG. 5, CTL assays for specific T cell lysis of target cells were performed using the Live/Dead cell mediated cytotoxicity method using flow cytometry. Patient-derived Peripheral Blood Monocyte Cells (PBMC) were cultured into DC ex vivo in the presence of GM-CSF and IL-4. After 5-6 days of differentiation into immature DC, specific peptides were added along with CD-40L to stimulate and develop mature DC. Post-maturation additional autologous PBMC were added and allowed to develop into CTL's. After 10 days cells were removed and mixed with autologous or allogeneic human lymphoma cells in culture to assess cell killing ability of CTL's. CTL were added to the target lymphoma cells in ratios ranging from 5:1 to 40:1 for 2 hours at 37° C. The analysis is based upon gating of labeled lymphoma cells to eliminate background from effector cells. Maximal cytotoxicity was simulated using ethanol-treated target cells. Spontaneous cytotoxicity represents target cells incubated in the absence of effector cells. Data represent mean percent specific lysis±S.E.M. of triplicate samples.

The data presented in FIG. 5 demonstrate that the invention elicits a strong cell mediated immune response was autologous CNS lymphoma cells. Thus, the invention is capable of stimulating an immune response against immune cells that express survivin. Using the same experimental approach we have demonstrated similar results against chronic lymphocytic leukemia (CLL). The data presented in FIG. 6 demonstrate that the invention is capable of stimulating an effective immune response against glioma in a clinically relevant in vivo mouse model. Thus, it will be apparent to those skilled in the art that, based on the foregoing data and description, the method of the present invention can stimulate an immune response against survivin-expressing cells, including cells of the immune system that express surivin, as well as cancer cells. It is expected that the invention will thus be useful for stimulating an effective cell mediated immune response against any type of survivin expressing cell in an individual and accordingly, inhibit the growth of such cells.

The invention has been described through specific embodiments. However, routine modifications to the compositions, methods and devices will be apparent to those skilled in the art and such modifications are intended to be covered within the scope of the invention.

We claim:

1. A method for stimulating an immune response against survivin expressing cells in an individual comprising administering to the individual a composition comprising a peptide of SEQ ID NO:4 (ENEPDLAQMFFCFKELEGWEPDD) or a fragment thereof, wherein the fragment comprises at least 9 contiguous amino acids of SEQ ID NO:4, and wherein the fragment comprises the sequence of SEQ ID NO:5 (QMFFCF).

2. The method of claim 1, wherein the survivin expressing cells are present in an individual who has rheumatoid arthritis.

3. The method of claim 1, wherein the survivin expressing cells are present in an individual who has multiple sclerosis.

4. The method of claim 1, wherein the peptide is conjugated to an immunogenic carrier protein.

5. The method of claim 1, wherein the peptide consists of the sequence of SEQ ID NO:6.

6. The method of claim 1, wherein the peptide in the composition is present in dendritic cells that have taken up the peptide.

7. The method of claim 1, wherein the survivin expressing cells are present in a joint in the individual.

* * * * *

```
                               SEQUENCE LISTING

<160> NUMBER OF SEQ ID NOS: 20

<210> SEQ ID NO 1
        <211> LENGTH: 142
        <212> TYPE: PRT
        <213> ORGANISM: human

<400> SEQUENCE: 1

Met Gly Ala Pro Thr Leu Pro Pro Ala Trp Gln Pro Phe Leu Lys Asp
        1               5                   10                  15

His Arg Ile Ser Thr Phe Lys Asn Trp Pro Phe Leu Glu Gly Cys Ala
                        20                  25                  30

Cys Thr Pro Glu Arg Met Ala Glu Ala Gly Phe Ile His Cys Pro Thr
                    35                  40                  45

Glu Asn Glu Pro Asp Leu Ala Gln Cys Phe Phe Cys Phe Lys Glu Leu
                50                  55                  60

Glu Gly Trp Glu Pro Asp Asp Pro Ile Glu Glu His Lys Lys His
        65                  70                  75                  80

Ser Ser Gly Cys Ala Phe Leu Ser Val Lys Lys Gln Phe Glu Glu Leu
                        85                  90                  95

Thr Leu Gly Glu Phe Leu Lys Leu Asp Arg Glu Arg Ala Lys Asn Lys
                    100                 105                 110

Ile Ala Lys Glu Thr Asn Asn Lys Lys Lys Glu Phe Glu Glu Thr Ala
                115                 120                 125

Lys Lys Val Arg Arg Ala Ile Glu Gln Leu Ala Ala Met Asp
            130                 135                 140

<210> SEQ ID NO 2
        <211> LENGTH: 140
        <212> TYPE: PRT
        <213> ORGANISM: mouse

<400> SEQUENCE: 2

Met Gly Ala Pro Ala Leu Pro Gln Ile Trp Gln Leu Tyr Leu Lys Asn
        1               5                   10                  15

Tyr Arg Ile Ala Thr Phe Lys Asn Trp Pro Phe Leu Glu Asp Cys Ala
                        20                  25                  30

Cys Thr Pro Glu Arg Met Ala Glu Ala Gly Phe Ile His Cys Pro Thr
                    35                  40                  45

Glu Asn Glu Pro Asp Leu Ala Gln Cys Phe Phe Cys Phe Lys Glu Leu
                50                  55                  60
```

```
Glu Gly Trp Glu Pro Asp Asp Asn Pro Ile Glu Glu His Arg Lys His
65                  70                  75                  80

Ser Pro Gly Cys Ala Phe Leu Thr Val Lys Lys Gln Met Glu Glu Leu
                85                  90                  95

Thr Val Ser Glu Phe Leu Lys Leu Asp Arg Gln Arg Ala Lys Asn Lys
            100                 105                 110

Ile Ala Lys Glu Thr Asn Asn Lys Gln Lys Glu Phe Glu Thr Ala
        115                 120                 125

Lys Thr Thr Arg Gln Ser Ile Glu Gln Leu Ala Ala
    130                 135                 140

<210> SEQ ID NO 3
<211> LENGTH: 23
<212> TYPE: PRT
<213> ORGANISM: human

<400> SEQUENCE: 3

Glu Asn Glu Pro Asp Leu Ala Gln Cys Phe Phe Cys Phe Lys Glu Leu
1               5                   10                  15

Glu Gly Trp Glu Pro Asp Asp
            20

<210> SEQ ID NO 4
<211> LENGTH: 23
<212> TYPE: PRT
<213> ORGANISM: artificial sequence
<220> FEATURE:
<223> OTHER INFORMATION: 23 amino acid peptide consisting of wild type
      survivin amino acids 49-71, but for a C to M alteration at amino
      acid position 57 of full length survivin (the C to M alteration
      is present at amino acid number 9 of this sequence

<400> SEQUENCE: 4

Glu Asn Glu Pro Asp Leu Ala Gln Met Phe Phe Cys Phe Lys Glu Leu
1               5                   10                  15

Glu Gly Trp Glu Pro Asp Asp
            20

<210> SEQ ID NO 5
<211> LENGTH: 6
<212> TYPE: PRT
<213> ORGANISM: artificial sequence
<220> FEATURE:
<223> OTHER INFORMATION: core survivin sequence with single change

<400> SEQUENCE: 5

Gln Met Phe Phe Cys Phe
1               5

<210> SEQ ID NO 6
<211> LENGTH: 15
<212> TYPE: PRT
<213> ORGANISM: artificial sequence
<220> FEATURE:
<223> OTHER INFORMATION: SVN53-67/M57 with C to M change

<400> SEQUENCE: 6

Asp Leu Ala Gln Met Phe Phe Cys Phe Lys Glu Leu Glu Gly Trp
1               5                   10                  15

<210> SEQ ID NO 7
<211> LENGTH: 8
<212> TYPE: PRT
<213> ORGANISM: human
```

<400> SEQUENCE: 7

Ser Ile Ile Asn Phe Glu Lys Leu
1               5

<210> SEQ ID NO 8
<211> LENGTH: 8
<212> TYPE: PRT
<213> ORGANISM: human

<400> SEQUENCE: 8

Ala Trp Gln Pro Phe Leu Lys Asp
1               5

<210> SEQ ID NO 9
<211> LENGTH: 8
<212> TYPE: PRT
<213> ORGANISM: human

<400> SEQUENCE: 9

Arg Ile Ser Thr Phe Lys Asn Trp
1               5

<210> SEQ ID NO 10
<211> LENGTH: 8
<212> TYPE: PRT
<213> ORGANISM: human

<400> SEQUENCE: 10

Ala Glu Ala Gly Phe Ile His Cys
1               5

<210> SEQ ID NO 11
<211> LENGTH: 8
<212> TYPE: PRT
<213> ORGANISM: human

<400> SEQUENCE: 11

Cys Phe Phe Cys Phe Lys Glu Leu
1               5

<210> SEQ ID NO 12
<211> LENGTH: 8
<212> TYPE: PRT
<213> ORGANISM: human

<400> SEQUENCE: 12

Ser Gly Cys Ala Phe Leu Ser Val
1               5

<210> SEQ ID NO 13
<211> LENGTH: 8
<212> TYPE: PRT
<213> ORGANISM: artificial sequence
<220> FEATURE:
<223> OTHER INFORMATION: SVN-L82 mutant peptide

<400> SEQUENCE: 13

Leu Gly Cys Ala Phe Leu Ser Val
1               5

<210> SEQ ID NO 14
<211> LENGTH: 8
<212> TYPE: PRT
<213> ORGANISM: human

```
<400> SEQUENCE: 14

Thr Leu Gly Glu Phe Leu Lys Leu
 1               5

<210> SEQ ID NO 15
<211> LENGTH: 10
<212> TYPE: PRT
<213> ORGANISM: artificial sequence
<220> FEATURE:
<223> OTHER INFORMATION: SVN55-64/57M mutant peptide

<400> SEQUENCE: 15

Ala Gln Met Phe Phe Cys Phe Lys Glu Leu
 1               5                  10

<210> SEQ ID NO 16
<211> LENGTH: 9
<212> TYPE: PRT
<213> ORGANISM: artificial sequence
<220> FEATURE:
<223> OTHER INFORMATION: SVN56-64/57M mutant peptide

<400> SEQUENCE: 16

Gln Met Phe Phe Cys Phe Lys Glu Leu
 1               5

<210> SEQ ID NO 17
<211> LENGTH: 8
<212> TYPE: PRT
<213> ORGANISM: artificial sequence
<220> FEATURE:
<223> OTHER INFORMATION: SVN-57-64/M57 mutant peptide

<400> SEQUENCE: 17

Met Phe Phe Cys Phe Lys Glu Leu
 1               5

<210> SEQ ID NO 18
<211> LENGTH: 15
<212> TYPE: PRT
<213> ORGANISM: human

<400> SEQUENCE: 18

Asp Leu Ala Gln Cys Phe Phe Cys Phe Lys Glu Leu Glu Gly Trp
 1               5                  10                  15

<210> SEQ ID NO 19
<211> LENGTH: 10
<212> TYPE: PRT
<213> ORGANISM: human

<400> SEQUENCE: 19

Ala Gln Cys Phe Phe Cys Phe Lys Glu Leu
 1               5                  10

<210> SEQ ID NO 20
<211> LENGTH: 9
<212> TYPE: PRT
<213> ORGANISM: human

<400> SEQUENCE: 20

Gln Cys Phe Phe Cys Phe Lys Glu Leu
 1               5
```